(12) United States Patent
Fujisato et al.

(10) Patent No.: US 7,745,105 B2
(45) Date of Patent: Jun. 29, 2010

(54) METHOD OF PREPARING SOFT TISSUE FOR A BIOLOGICAL SCAFFOLD BY LYOPHILIZING, HEATING AND ELASTASE TREATMENT

(75) Inventors: Toshiya Fujisato, Suita (JP); Dohiko Terada, Suita (JP); Kazuya Sawada, Suita (JP); Takeshi Nakatani, Suita (JP)

(73) Assignee: Japan Health Sciences Foundation, Tokyo (JP)

( * ) Notice: Subject to any disclaimer, the term of this patent is extended or adjusted under 35 U.S.C. 154(b) by 666 days.

(21) Appl. No.: 11/798,491

(22) Filed: May 14, 2007

(65) Prior Publication Data

US 2008/0027562 A1    Jan. 31, 2008

(30) Foreign Application Priority Data

Jul. 31, 2006    (JP)    ............................. 2006-207384

(51) Int. Cl.
*A01N 1/00*    (2006.01)
*A61F 2/04*    (2006.01)

(52) U.S. Cl. .......................................... 435/1.1; 600/36
(58) Field of Classification Search ....................... None
See application file for complete search history.

(56) References Cited

U.S. PATENT DOCUMENTS

2006/0110720 A1    5/2006    Fujisato et al.

FOREIGN PATENT DOCUMENTS

JP    2004-097552 A2    4/2004

*Primary Examiner*—Sandra E Saucier
(74) *Attorney, Agent, or Firm*—Millen, White, Zelano, Branigan, P.C.

(57) ABSTRACT

A method for preparing a scaffold material for use in the prosthesis therapy is disclosed. The method comprises (a) lyophilizing a segment of native soft tissue of mammalian origin, heating the lyophilized tissue at a temperature of 100-200° C., and incubating the tissue with elastase to selectively remove elastin leaving the extracellular components mainly comprised of collagen.

10 Claims, 3 Drawing Sheets

(a)            (b)

METHOD OF PREPARING SOFT TISSUE FOR A BIOLOGICAL SCAFFOLD BY LYOPHILIZING, HEATING AND ELASTASE TREATMENT

FIELD OF THE INVENTION

The present invention relates to a method for preparing biological scaffold materials for use in the prosthesis of impaired organs such as heart valves or vascular vessels.

Prosthetic surgery is aimed to repair impaired organs by replacing with artificial devices. To this end scaffold materials are implanted and allowed to reconstruct the organ. Currently porcine or bovine tissues have been used as the scaffold material after treating with glutaraldehyde. However, these materials are susceptible to calcification in vivo and, therefore, their life is limited to less than about 15 years in case of heart valves. Glutaraldehyde-treated porcine or bovine tissues are used also as vascular grafts. In addition to the limited life due to calcification, they have another disadvantage when used as vascular grafts which require to have sufficient elasticity and tensile strength. The treatment with glutaraldehyde greatly decreases the elasticity and tensile strength of the native tissue from which the scaffold material is made.

Artificial vascular grafts made of biodegradable polymers such as polylactic acid have been clinically used in children. However, constriction and other adverse effects have been reported. In addition, the biodegradable vascular grafts cannot be used in the artery system because of possible puncture due to the hydrolysis of the polymer.

It is known to prepare implantable scaffold materials by decellularizing biological tissues with enzymes or surfactants to obtain extracellular matrix components. However, the decellularized tissues as such are not only susceptible to calcification but do not retain sufficient strength properties to withstand relatively high pressures in the body.

Accordingly, a need remains to exist for a biological scaffold material which is biocompatible in terms of immunogenicity and thromboticity, which may be eventually decomposed in the living body but persistent until the target organ is reconstructed, and which is not susceptible to calcification.

SUMMARY OF THE INVENTION

The above and other needs may be met by the present invention. The present invention provides a method for preparing a scaffold material for use in the prosthesis therapy comprising the steps of:

(a) lyophilizing a segment of native soft tissue of mammalian origin;

(b) heating the lyophilized tissue under vacuum at a temperature between 100° C. and 200° C. whereby partial crosslinking and fixation of proteins take place; and (c) incubating the tissue with elastase to selectively remove elastin from the tissue leaving extracellular components mainly comprised of collagen.

In one embodiment of the present invention, the native tissue is decellularized before lyophilization by applying ultrahigh hydrostatic pressure to the tissue in a liquid medium.

Elastin is known to be prone to calcification of grafts in the living body. Accordingly, it is preferable for graft materials to contain elastin as low as possible. Since elastin and collagen are major structural proteins, removal of elastin alone is not sufficient to provide graft materials satisfying with other requisite properties, particularly mechanical strength.

Partial crosslinking and fixation of proteins serve to preserve the mechanical strength of the starting native tissue to a large extent. Heating of lyophilized tissue under vacuum induces dehydration-condensation reactions between amino groups and carboxyl and/or hydroxyl groups present in the protein. However, the degree of crosslinking is less than the glutaraldehyde crosslinking and limited to an extent which does not interfere with enzymatic digestion of elastin.

Decellularization of tissue before lyophilization and heat treatment not only reduces the immunogenicity of the scaffold but also further improves the biodynamic properties such as tensile strength thereof.

BRIEF DESCRIPTION OF THE ACCOMPANYING DRAWINGS

BEST MODE FOR CARRYING OUT THE INVENTION

Figure 1:
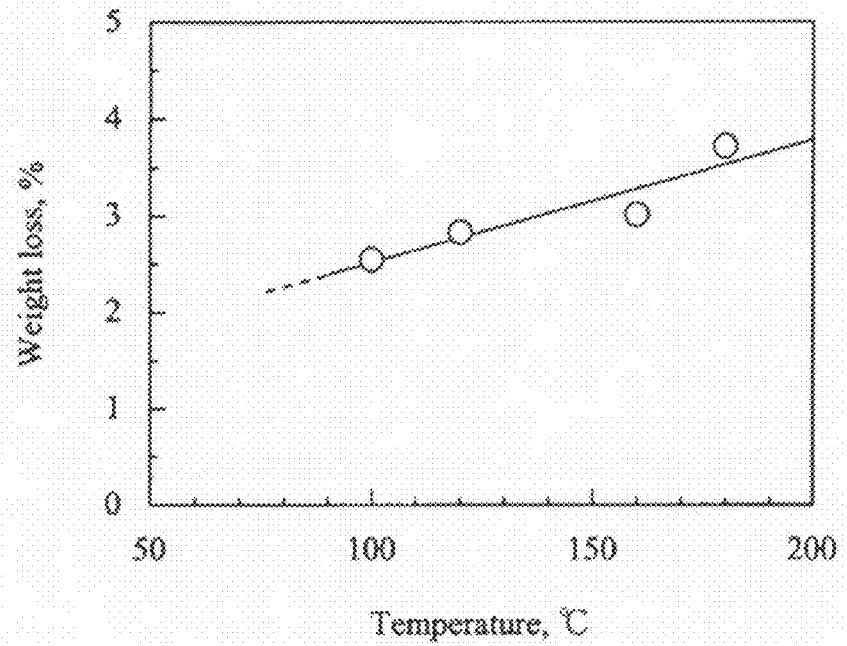
FIG. 1 is a graph showing the relationship between the weight loss of lyophilized tissue and the temperature when heating under vacuum for 24 hours.

The method of the present invention is applicable to native soft tissues of mammalian origin. They are fibrous structural tissues containing collagen fibers and elastin fibers. The tissue may be autologous, allogeneic or xenogeneic. Porcine or bovine organs and part thereof such as hearts, heart valves and blood vessels are preferable.

Partial crosslinking of the tissue is carried out by heating the lyophilized tissue under vacuum. This involves a dehydration-condensation reaction between the amino group and the carboxyl or hydroxyl group. These groups are possessed by the amino acid residues constituting the tissue protein. For example, amino group is contained in lysine residue, carboxyl group is contained in glutamic or aspartic residue, and hydroxyl group is contained in serine or threonine residue.

Lyophilized tissue is heated under vacuum at a temperature between 100° C. and 200° C. to crosslink and fix the tissue partially. The dehydration-condensation reaction proceeds only partially during the heating of lyophilized tissue because water or other heat conductive liquids is not present between molecules. It is preferable to continue the heating until the weight loss reaches at 2-3%. The exact heating time varies with the particular temperature employed. For example, the weight loss in the above range may be reached at 120° C. for about 24 hours. The higher temperature, the shorter the required time.

The heat-treated tissue is then incubated with elastase to selectively remove elastin therefrom. The reaction is carried out at an optimum pH of 7.5-8.5. A satisfactory result was obtained when the reaction was carried out at a pH of 8.0 in tris buffer at 37° C. It is possible, of course, to carry out the reaction at a pH recommended by the manufacturer of elastase using any buffer other than tris. The enzyme concentration is generally 300-10,000 U/L, preferably 600 U/L. The reaction time is generally 1-7 days, preferably 2-7 days at 37° C. After the reaction, the tissue is well rinsed with purified water, saline or a buffer solution and preserved in PBS or other preservation solutions until use.

In an alternative embodiment, the native tissue of mammarian origin is first decellularized before the enzymatic removal of elastin. Preferably the decellularization is carried out by placing the tissue in a fluid and applying ultrahigh hydrostatic pressure. This decellularization method is disclosed in JP 200497552A and US 2006/0110720A1, of which disclosures are incorporated herein by reference. This method is particularly advantageous because it enables to remove cellular components while keeping the structure and biomechanical properties intact and also to accomplish sterilization and virus inactivation simultaneously. For the purpose of the present invention, preferred conditions are found to be the application of ultrahigh hydrostatic pressure of 5,000-10,000 atoms for 10 minutes in a sterile water. After the application of ultrahigh static pressure, the tissue is washed with pure water, saline or a buffer solution to wash out released cells and then subjected to lyophilization as the first embodiment. The pre-treated tissue in this manner enhances the biodynamic properties, particularly mechanical strength of the resulting scaffold material.

The scaffold material prepared by the inventive methods is mainly comprised of collagen. It is this collagen that has been crosslinked by the heat treatment of lyophilized tissue under vacuum. Therefore, the heat treatment does not essentially affect enzymatic removal of elastin because elastin consists mainly of electrically neutral non-aromatic amino acid residues and free from amino acid residues having mutually crosslinkable groups. In contrast, collagen has such mutually crosslinkable groups. However, the crosslinking takes place only partially by virtue of the reaction conditions employed and collagen remains biodegradable in vivo by the action of collagenase.

Example 1

Porcine aorta purchased from Japan Farm Co., Ltd. was cut into tubular segments, lyophilized, and heated at 100° C., 120° C., 160° C., or 180° C. for a constant period of time of 24 hours in a vacuum chamber. The weight of the tissue segment was measured before and after the heat treatment to determine percent weight loss at varying temperatures. The results are shown in the graph of FIG. 1. The best result was obtained for the tissue heated at 120° C. for 24 hours when treating with elastase as described below.

Separately, an enzyme solution was prepared from a commercially available elastase preparation (3.95 U/mg, Funakoshi) by dissolving the enzyme in 0.0 M tris buffer (pH 8.0) to a concentration of 150 mg/L (0.57 U/ml), followed by the addition of 0.01M $CaCl_2$ and 0.02% sodium azide.

The tissue treated at 120° C. for 24 hours was placed in the above elastase solution, incubated at 37° C. for 72 hours, and rinsed with physiological saline.

Example 2

Porcine aorta segments as used in Example 1 were decellularized by placing in an ultrahigh pressure apparatus (Dr. SHEF available from Kobe Steel Ltd.) together with sterile water and applied a hydrostatic pressure of 10,000 atms for 10 minutes. The decellularized tissue was thoroughly washed with sterile water.

The procedure of Example 1 was repeated with the decellularized tissue under exactly the same conditions to prepare a scaffold material.

Figure 2:
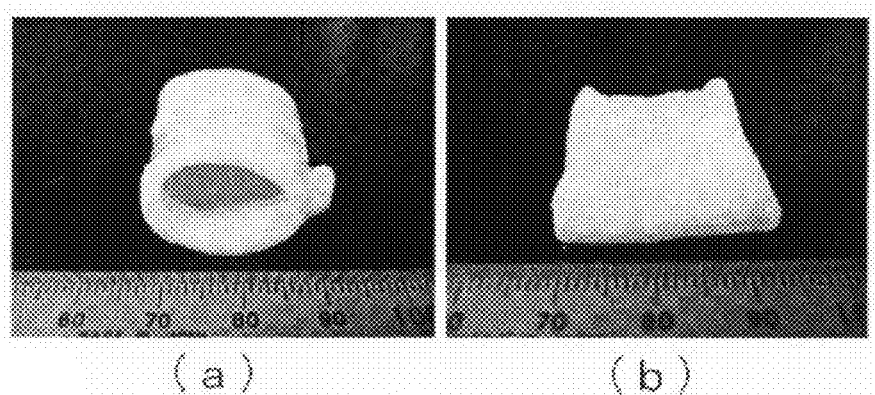
FIG. 2 shows a segment of porcine aorta before and after the treatment of the present invention in (a) and (b), respectively.

In FIG. 2, (a) is a photograph of native porcine aorta segment and (b) is a similar photograph of porcine aorta segment treated in Example 1. As seen, the tubular shape of native aorta was maintained after the treatment with heat and then with elastase.

Figure 3:
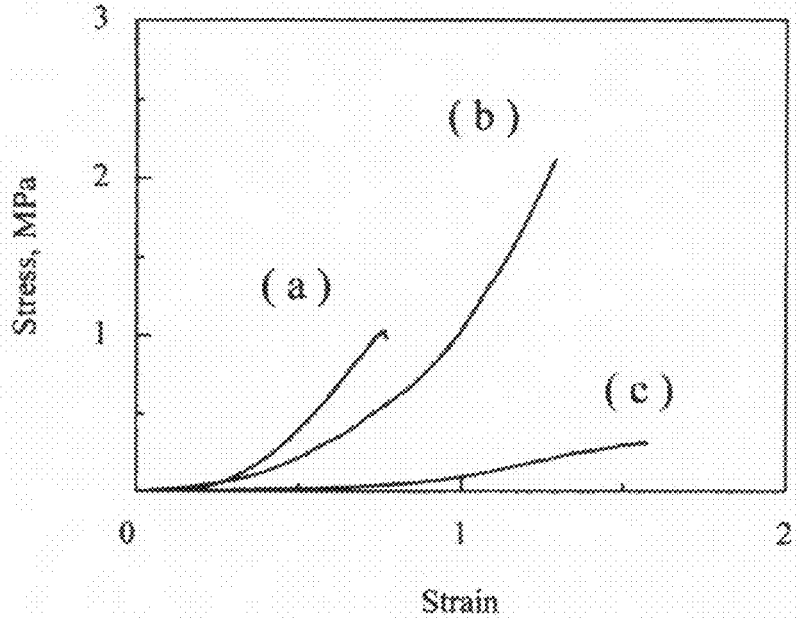
FIG. 3 shows the stress vs. strain curve of the scaffold prepared by the method of the present invention from porcine aorta (a) in comparison with those of untreated porcine aorta (b) and untreated porcine pulmonary artery (c).

The scaffold material prepared in Example 1 was tested for strength properties along the circumferential direction in comparison with native porcine aorta and native porcine pulmonary artery. FIG. 3 shows the stress vs. strain curve (a) of the scaffold of Example 1, in comparison with the stress vs. strain curve of native porcine aorta (b) and the stress vs. strain curve of native porcine pulmonary artery (c). The tensile strength of the aorta treated by the present invention is, as seen, lower than the native aorta but higher than native pulmonary artery. This means that the tensile strength of the aorta treated by the present invention is higher than the native pulmonary vein implying that the scaffold may be implanted to the aorta site instead of autologous pulmonary valve in the Ross operation for children.

Figure 4:
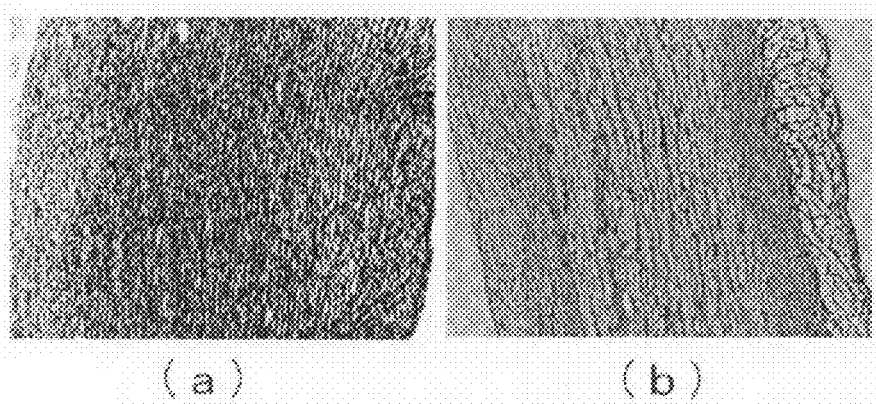
FIG. 4 shows histographic pictures of stained porcine aorta tissue before and after treating by the method of the present invention (a) and (b), respectively.

FIG. 4 is histographic pictures of the porcine aorta tissue stained by the Elastica von Gieson method before and after the treatment of the present invention. As seen, elastin fibers are abundantly present throughout the vessel wall in the native tissue (a), while elastin fibers have been removed almost completely leaving extracellular components mainly comprised of collagen fibers in the treated tissue (b).

Figure 5:
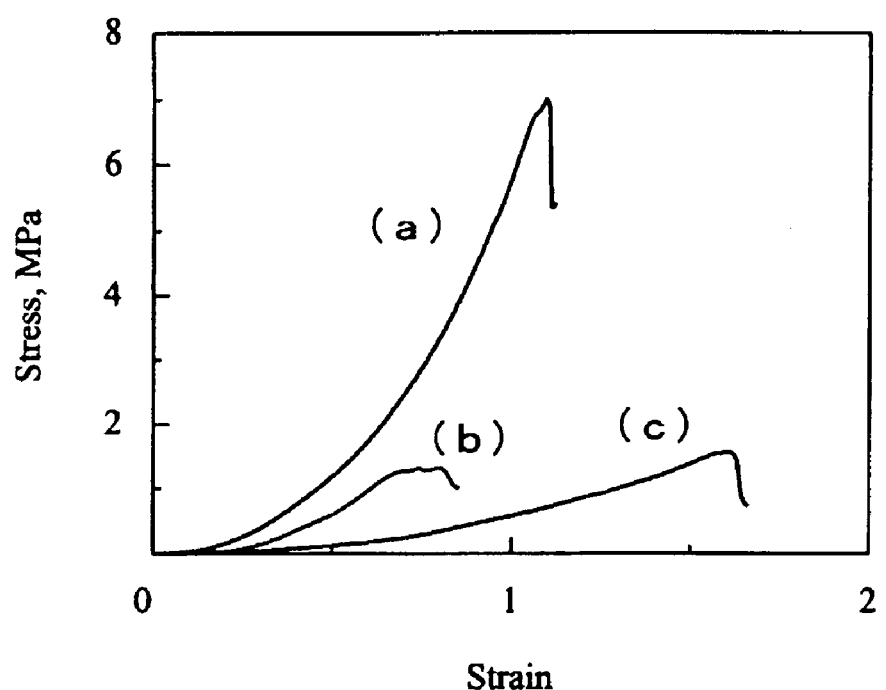
FIG. 5 shows the stress vs. strain curves (a) and (b) of the scaffold materials prepared in Examples 1 and 2, respectively in comparison with the stress vs. strain curve of untreated porcine aorta (c).

FIG. 5 shows the stress vs. strain curves similar to FIG. 3 in which (a) is the stress vs. strain curve of the scaffold prepared in Example 2 (with decellularization), (b) is the stress vs. strain curve of the scaffold prepared in Example 1. (without decellularization), and (c) is the curve of native porcine aorta.

As seen, the tensile strength of the scaffold may be increased to as much as about 6 times by the decellularization of the tissue by the application of ultrahigh hydrostatic pressure compared to the scaffold prepared without decellularization.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Japanese application No. 2006-2007384, filed Jul. 31, 2006 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for preparing a scaffold material for use in the prosthesis therapy comprising the steps of:
   (a) lyophilizing a segment of native soft tissue of mammalian origin;

(b) heating the lyophilized tissue under vacuum at a temperature between 100° C. and 200° C. whereby partial crosslinking and fixation of proteins take place; and (c) incubating the tissue with elastase to selectively remove elastin leaving extracellular components mainly comprised of collagen.

2. The method according to claim 1 wherein said soft tissue is a connective tissue comprising elastin and collagen.

3. The method according to claim 1 wherein said step (b) is carried out at a temperature of 120° C. for 24 hours.

4. The method according to claim 1 wherein said step (c) is carried out in a buffer adjusted to an optimum pH of elastase.

5. The method according to claim 4 wherein said buffer is a tris buffer having a pH from 7.5 to 8.5.

6. The method according to claim 1 further including, following the step (c), rinsing the tissue with water, saline or a buffer solution.

7. The method according to claim 1 further including, prior to the step (a), removing cellular components from the tissue at least partially by applying ultrahigh hydrostatic pressure to the tissue in a fluid and washing out the cellular components.

8. The method according to claim 7 wherein said ultrahigh hydrostatic pressure is within the range between 5,000 and 15,000 atms.

9. The method according to claim 1 wherein the scaffold is for reconstruction of vascular vessels or heart valves.

10. The method according to claim 7 wherein the scaffold is for reconstruction of vascular vessels or heart valves.

* * * * *